United States Patent [19]  
Gottesman

[11] 4,034,007  
[45] July 5, 1976

[54] PROCESS FOR THE PRODUCTION OF HALOGENATED AROMATIC CARBOXYLIC ACIDS

[75] Inventor: Roy Tully Gottesman, Glen Rock, N.J.

[73] Assignee: Tenneco Chemicals, Inc., Saddle Brook, N.J.

[22] Filed: Jan. 7, 1972

[21] Appl. No.: 216,279

[52] U.S. Cl. .................................. 260/524 R
[51] Int. Cl.² .................................. C07C 51/33
[58] Field of Search ........................ 260/524 R

[56] References Cited

UNITED STATES PATENTS

| | | | |
|---|---|---|---|
| 3,452,087 | 6/1969 | Patton et al. | 260/524 |
| 3,686,293 | 8/1972 | Gualdi et al. | 260/524 |

FOREIGN PATENTS OR APPLICATIONS

| | | | |
|---|---|---|---|
| 652,718 | 11/1962 | Canada | 260/524 |

Primary Examiner—Paul J. Killos  
Attorney, Agent, or Firm—Evelyn Berlow

[57] ABSTRACT

Halogenated aromatic carboxylic acids are prepared in high yield by the liquid phase oxidation of halogenated alkylbenzenes in the presence of a heavy metal oxidation catalyst and a vicinal epoxide having from 2 to 8 carbon atoms.

8 Claims, No Drawings

PROCESS FOR THE PRODUCTION OF HALOGENATED AROMATIC CARBOXYLIC ACIDS

This invention relates to a process for the production of halogenated aromatic carboxylic acids. More particularly, it relates to a process for the liquid phase oxidation of halogen-substituted alkylbenzenes to the corresponding halogenated aromatic carboxylic acids.

It was reported in German Pat. No. 767,366 that a 50 percent yield of o-chlorobenzoic acid was obtained when o-chlorotoluene was contacted with oxygen in the presence of cobalt naphthenate at 145° C. for 10 hours. Attempts to repeat this oxidation have been unsuccessful; in no case has the yield of o-chlorobenzoic acid been greater than 1 percent. A process in which an 86 percent yield of o-chlorobenzoic acid was said to be obtained when o-chlorotoluene was contacted with oxygen in the process of cobalt acetate, hydrogen bromide, and acetic acid has been reported (Can. J. Chem. 43, 1306–17 (1965)). Here again it has been impossible to duplicate the reported yield. When the oxidation was carried out under the conditions described in this paper, a 43 percent yield of o-chlorobenzoic acid was obtained, and it was necessary to distill the reaction mixture to recover the acetic acid. When this oxidation was carried out in the absence of acetic acid, the conversion of o-chlorotoluene to o-chlorobenzoic acid was 4 percent. It is believed that the low conversions obtained when the reported procedures were repeated were the result of slight decomposition of the o-chlorotoluene and the subsequent inactivation of the heavy metal oxidation catalyst by traces of free hydrogen chloride in the reaction mixture. It is known that inorganic acid acceptors, such as alkali metal and alkaline earth metal oxides, hydroxides, and carbonates, can be used to react with and neutralize hydrogen halide as it is produced during a reaction. These inorganic compounds and the resulting halide salts, however, are usually insoluble in the organic reaction mixture. Because they are difficult to keep evenly dispersed in the reaction mixture, they often cause plugs or unwanted deposits in the apparatus. In addition the strongly basic properties of these acid acceptors may affect adversely the organic reaction.

In accordance with this invention, it has been found that halogen-substituted alkylbenzenes can be converted to the corresponding halogenated aromatic carboxylic acids by liquid phase oxidation in the presence of a heavy metal oxidation catalyst and an acid acceptor that is a vicinal epoxide compound having from 2 to 8 carbon atoms.

The compounds that can be oxidized to carboxylic acids by the process of this invention have the structural formula

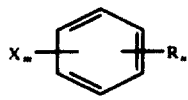

wherein X represents chlorine, bromine, iodine, or fluorine; R represents an alkyl having from 1 to 4 carbon atoms or a haloalkyl group having from 1 to 4 carbon atoms and from 1 to 4 halogen atoms; and $m$ and $n$ each represents a number in the range of 1 to 5, the sum of $m$ and $n$ being in the range of 2 to 6. Illustrative of these compounds are the following: o-, m-, and p-chlorotoluene; 2,4-, 3,4-, 2,3-, and 2,6-dichlorotoluenes; 2,3,6-, 2,3,4-, and 2,4,6-trichlorotoluenes; 2,3,4,5- and 2,3,5,6-tetrachlorotoluenes; pentachlorotoluene; o-, m-, and p-bromotoluene; 2,4-, 3,4-, 2,3-, and 2,6-dibromotoluenes; 2,3,6-, 2,3,4-, and 2,4,6-tribromotoluenes; 2,3,4,5- and 2,3,5,6-tetrabromotoluenes; pentabromotoluene; the iodtoluenes and fluorotoluenes corresponding to the aforementioned chlorotoluenes; 2-chloro-4-bromotoluene, 2-chloro-6-iodotoluene; mono-, di-, tri-, and tetrachloroxylenes; mono-, di-, tri-, and tetrabromoxylenes; xylylene dichloride; xylylene dibromide; 6-bromopseudocumene; 6-iododurene; 1,2,3,4-tetraethyl-6-chlorobenzene; chloropentamethylbenzene; and the like.

Particularly satisfactory results have been obtained using as the starting material in this process a halogenated alkylbenzene that has 1 or 2 methyl groups and from 1 to 3 chlorine atoms as substituents on the aromatic nucleus. Examples of these halogenated alkylbenzenes include o-, m-, and p-chlorotoluene, 2,4-dichlorotoluene, 2,3,4-trichlorotoluene, 4-chloro-o-xylene, 2-chloro-p-xylene, 3,6-dichloro-o-xylene, and 2,3,5-p-xylene.

When a halogenated toluene is oxidized by the process of this invention, the product is a chlorobenzoic acid. When the starting material is a compound that has two or more alkyl groups as substituents on the aromatic nucleus, the conditions under which the oxidation is carried out can be adjusted to yield either a monocarboxylic acid, a dicarboxylic acid or polycarboxylic acid, or a mixture of monocarboxylic and di- or polycarboxylic acids. For example, depending upon the reaction conditions employed, 2-chloro-p-xylene can be converted to a methylchlorobenzoic acid, to 2-chloroterephthalic acid, or to a mixture of these acids.

In the process of this invention, a halogenated alkylbenzene is introduced into a reactor which is preferably a column. An oxygen-containing gas, for example, air or oxygen, is fed into the bottom of the reactor and allowed to bubble through the feedstock. The oxidation is effected in the presence of an epoxide as hereinafter defined and a heavy metal oxidation catalyst, such as cobalt acetate, cobalt octoate, cobalt benzoate, cobalt naphthenate, manganese acetate, manganese octoate, manganese benzoate, manganese naphthenate, vanadium octoate, and the like. The amount of oxidation catalyst used is generally in the range of about 0.01 percent to 5 percent and preferably 0.1 percent to 1 percent of the weight of halogenated alkylbenzene in the reactor. The oxidation reaction is carried out at a temperature between about 130° C. and the boiling point of the halogenated alkylbenzene at a pressure in the range of about 10 p.s.i. to 75 p.s.i. It is preferably carried out at a temperature between 150° C. and the boiling point of the halogenated alkylbenzene at atomspheric pressure. The oxidation reaction is usually discontinued when about 40 percent to 50 percent of the feedstock has undergone oxidation. The halogenated carboxylic acid is recovered from the oxidation mixture and purified by known procedures. Unreacted halogenated alkylbenzene may be recovered from the oxidation mixture and used in a subsequent oxidation.

The epoxides that can be used in the process of this invention are vicinal epoxides having from 2 to 8 carbon atoms. They include alkylene oxides, such as ethylene oxide, propylene oxide, isobutylene oxide, 1,2-pentene oxide, diisobutylene oxide, and butadiene dioxide; closed chain or cyclic oxides, such as cyclohexane oxide and vinylcyclohexene oxide; and substituted epoxides including halogen derivatives and epoxy ethers, such as epichlorohydrin, epibromohydrin, butyl glycidyl ether, phenyl glycidyl ether, diglycidyl ether, allyl ether, and styrene oxide. The preferred epoxides are those of relatively low molecular weight and boiling point, such as epichlorohydrin, ethylene oxide, propylene oxide, and butylene oxide.

Only a small amount of the vicinal epoxide need be present in the reaction mixture during the oxidation. As little as 0.001 mole of epoxide per mole of halogenated alkylbenzene will result in a substantial improvement in the yield of the halogenated aromatic carboxylic acid. In most cases about 0.02 mole to 1.0 mole of the epoxide is used per mole of halogenated alkylbenzene. More epoxide can be used, but the use of such an excess may cause undue dilution of the reaction mixture. If desired, the epoxide may be diluted with an organic solvent which is unreactive in the process. All of the epoxide may be present at the start of the reaction, or it may be added incrementally to the reaction mixture throughout the oxidation reaction. Alternatively, the air or oxygen may be sparged through the epoxide in order to carry a small amount of the epoxide continuously into the reactor.

In addition to removing trace amounts of hydrogen halide from the reaction mixture and allowing the oxidation reaction to proceed statisfactorily, the use of the vicinal epoxides also results in the formation of products having better color and in many cases higher purity than do those obtained by the previously-known processes. This process has the added advantage of minimizing corrosion of the metal parts that are often used in the cooler upper sections of an oxidation column, especially since water is formed as a by-product of the oxidation.

The invention is further illustrated by the following examples.

EXAMPLE 1

The oxidation reaction was carried out in a jacketed glass column equipped with a sintered glass sparger, a condenser, and a Dean-Stark water trap.

Into the column were charged 453 grams (3.58 moles) of o-chlorotoluene, 2.25 grams of cobalt octoate (6% Co), and 1.0 gram of epichlorohydrin. The reaction mixture was heated to 155° C. and maintained at that temperature while oxygen was bubbled through it at the rate of 300 ml./min. An additional 1.0 gram of epichlorohydrin was added to the reaction mixture every two hours during the oxidation. Throughout the reaction period, the gases leaving the column remained non-acidic. At the end of 14 hours, when 35 grams of water had been collected, the reaction mixture was removed from the column, cooled to 75° C. and extracted with 600 grams of 10 percent aqueous sodium hydroxide solution. The layers that formed were separated. The aqueous layer was diluted with water to a volume of 1500 ml. and then acidified with hydrochloric acid. The o-chlorobenzoic acid that precipitated was collected, washed with water, and dried. There was obtained 177 grams (1.135 moles) of o-chlorobenzoic acid. The conversion of o-chlorotoluene to o-chlorobenzoic acid was 43 percent. The yield of o-chlorobenzoic acid, based on o-chlorotoluene reacted, was 73.8 percent.

When the organic layer was distilled, 258 grams (2.04 moles) of o-chlorotoluene was recovered.

EXAMPLE 2

Into the column described in Example 1 were charged 453 grams (3.58 moles) of o-chlorotoluene, 2.25 grams of cobalt octoate (6% Co), and 2.25 grams of epichlorohydrin. The reaction mixture was heated to 155° C. and maintained at that temperature while oxygen that had been sparged through epichlorohydrin was bubbled through it at the rate of 200 ml./min. Throughout the reaction period, the gases leaving the reactor remained non-acidic. At the end of 23 hours, the reaction was removed from the column, cooled to 75° C., and the extracted with 600 grams of 10 percent aqueous sodium hydroxide solution. The layers that formed were separated. The aqueous layer was diluted with water to a volume of 1500 ml. and then acidified with hydrochloric acid. The o-chlorobenzoic acid that precipitated was collected, washed with water, and dried. There was obtained 180 grams (1.55 moles) of o-chlorobenzoic acid. The conversion of o-chlorotoluene to o-chlorobenzoic acid was 14 percent. The yield of o-chlorobenzoic acid, based on o-chlorotoluene reacted, was 78.6 percent.

Distillation of the organic layer yielded 267 grams (2.11 moles) of o-chlorotoluene.

COMPARATIVE EXAMPLE

To the reactor described in Example 1 were charged 453 grams (3.58 moles) of o-chlorotoluene and 2.25 grams of cobalt octoate (Cobalt content — 6%). The reaction mixture was heated to 155° C. and maintained at that temperature while oxygen was bubbled through it. The gases leaving the reactor were acidic after one hour. The run was discontinued after six hours because little or no oxidation had taken place in this time as indicated by absence of evolved water. Workup of the reaction mixture yielded no o-chlorobenzoic acid.

Each of the other halogenated toluenes, halogenated xylenes, xylylene dihalides, and halogenated polyalkylbenzenes disclosed herein can also be converted to the corresponding armoatic carboxylic acid by means of the process of this invention.

The terms and expressions which have been employed are used as terms of description and not of limitation. There is no intention in the use of such terms and expressions of excluding any equivalents of the features shown and described or portions thereof, but it is recognized that various modifications are possible within the scope of the invention claimed.

What is claimed is:

1. In the process for the production of halogenated aromatic carboxylic acids which comprises contacting a halogenated alkylbenzene having the structural formula

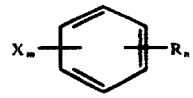

wherein X represents a halogen atom; R represents an alkyl group having from 1 to 4 carbon atoms or a haloalkyl group having from 1 to 4 carbon atoms and from 1 to 4 halogen atoms; and $m$ and $n$ each represents a number in the range of 1 to 5, the sum of $m$ and $n$ being in the range of 2 to 6, with an oxygen-containing gas in the presence of about 0.01 percent to 5 percent, based on the weight of the halogenated alkylbenzene, of a heavy metal oxidation catalyst selected from the group consisting of cobalt, manganese, and vanadium salts of alkanoic acids having 1 to 8 carbon atoms, benzoic acid, and naphthenic acids at a temperature between about 130° C. and the boiling point of said halogenated alkylbenzene and at a pressure in the range of about 10 p.s.i. to 75 p.s.i., the improvement that comprises carrying out the oxidation in the presence of at least 0.001 mole per mole of halogenated alkylbenzene of epichlorohydrin.

2. The process of claim 1 wherein the oxidation is carried out in the presence of 0.02 mole to 1.0 mole of epichlorohydrin per mole of halogenated alkylbenzene.

3. The process of claim 1 wherein epichlorohydrin is added incrementally to the reaction mixture throughout the oxidation reaction.

4. The process of claim 1 wherein epichlorohydrin is added continuously to the reaction mixture throughout the oxidation reaction.

5. The process of claim 1 wherein the halogenated alkylbenzene has the structural formula

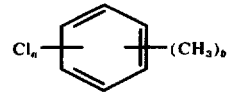

wherein $a$ represents a number in the range of 1 to 3 and $b$ represents a number in the range of 1 to 2.

6. The process of claim 1 wherein the halogenated alkylbenzene is o-chlorotoluene.

7. The process of claim 1 wherein the oxidation is carried out at a temperature between 150° C. and the boiling point of the halogenated alkylbenzene at atmospheric pressure.

8. The process of claim 1 wherein the oxidation is carried out in the presence of 0.1 percent to 1 percent, based on the weight of the halogenated alkylbenzene, of the heavy metal oxidation catalyst.

* * * * *